US012589061B2

(12) United States Patent
Yutaka et al.

(10) Patent No.: US 12,589,061 B2
(45) Date of Patent: Mar. 31, 2026

(54) METHOD FOR PRODUCING SILICA PARTICLES AND THEIR USE IN COSMETIC COMPOSITIONS

(71) Applicant: Momentive Performance Materials Japan LLC, Tokyo (JP)

(72) Inventors: Horie Yutaka, Kanagawa (JP); Benjamin Falk, Tarrytown, NY (US); Qinghua Li, Kanagawa (JP); Amar Pawar, Tarrytown, NY (US); Koji Suenaga, Gunma (JP)

(73) Assignee: MOMENTIVE PERFORMANCE MATERIALS JAPAN LLC, Tokyo (JP)

( * ) Notice: Subject to any disclaimer, the term of this patent is extended or adjusted under 35 U.S.C. 154(b) by 155 days.

(21) Appl. No.: 17/307,755

(22) Filed: May 4, 2021

(65) Prior Publication Data

US 2022/0354757 A1     Nov. 10, 2022

(51) Int. Cl.
| | |
|---|---|
| *A61K 8/25* | (2006.01) |
| *A61K 8/02* | (2006.01) |
| *A61K 8/58* | (2006.01) |
| *A61Q 1/06* | (2006.01) |
| *A61Q 1/08* | (2006.01) |
| *A61Q 1/10* | (2006.01) |
| *A61Q 1/12* | (2006.01) |
| *A61Q 5/02* | (2006.01) |
| *A61Q 5/06* | (2006.01) |
| *A61Q 5/12* | (2006.01) |
| *A61Q 9/02* | (2006.01) |
| *A61Q 11/00* | (2006.01) |
| *A61Q 15/00* | (2006.01) |
| *A61Q 17/00* | (2006.01) |
| *A61Q 19/00* | (2006.01) |
| *A61Q 19/10* | (2006.01) |

(52) U.S. Cl.
CPC ................ *A61K 8/25* (2013.01); *A61K 8/025* (2013.01); *A61K 8/585* (2013.01); *A61Q 19/00* (2013.01); *A61K 2800/412* (2013.01); *A61K 2800/48* (2013.01); *A61K 2800/52* (2013.01); *A61K 2800/522* (2013.01); *A61K 2800/524* (2013.01); *A61Q 1/06* (2013.01); *A61Q 1/08* (2013.01); *A61Q 1/10* (2013.01); *A61Q 1/12* (2013.01); *A61Q 5/02* (2013.01); *A61Q 5/06* (2013.01); *A61Q 5/12* (2013.01); *A61Q 9/02* (2013.01); *A61Q 11/00* (2013.01); *A61Q 15/00* (2013.01); *A61Q 17/00* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,837,011 | A | 6/1989 | Macchio et al. |
| 6,004,584 | A | 12/1999 | Peterson et al. |
| 6,231,955 | B1 | 5/2001 | Endo |
| 2003/0108580 | A1 | 6/2003 | Hasenzahl et al. |
| 2004/0161389 | A1 | 8/2004 | Gallis et al. |
| 2005/0261380 | A1 | 11/2005 | Suzuki et al. |
| 2011/0110995 | A1 | 5/2011 | Hasegawa et al. |
| 2019/0232252 | A1 | 8/2019 | Skinley et al. |

FOREIGN PATENT DOCUMENTS

| | | |
|---|---|---|
| CN | 112334196 A | 2/2021 |
| DE | 10153077 A1 | 5/2003 |
| JP | S 62260712 A | 11/1987 |
| JP | S 63103812 A | 5/1988 |
| JP | S 63-297313 A | 12/1988 |
| JP | H 5-43420 A | 2/1993 |
| JP | H11349707 A | 12/1999 |
| JP | 2001302227 A | 10/2001 |
| JP | 2005-60263 A | 3/2005 |
| JP | 2007084606 A | 4/2007 |
| JP | 5025259 B2 | 9/2012 |
| JP | 2017057094 A | 3/2017 |
| JP | 2017512132 A | 5/2017 |
| JP | 2018150226 A | 9/2018 |
| JP | 2020111526 A | 7/2020 |
| WO | WO 03037287 A1 | 5/2003 |
| WO | WO-2013062105 A1 | 5/2013 |
| WO | WO-2019241323 A1 | 12/2019 |

OTHER PUBLICATIONS

English translation of JPS63103812A (2023).*
Extended European Search Report for EP Application No. 21199540. 2, European Patent Office, Munich, Germany, mailed on Mar. 23, 2022, 12 pages.
Haussmann, M., et al., "Thermal degradation of polymethylsilsesquioxane and microstructure of the derived glasses," Journal of Analytical and Applied Pyrolysis 91:224-231, Elsevier B.V., Netherlands (Feb. 2011).

* cited by examiner

*Primary Examiner* — Anna R Falkowitz
*Assistant Examiner* — Garen Gotfredson
(74) *Attorney, Agent, or Firm* — Sterne, Kessler, Goldstein & Fox P.L.L.C.

(57) ABSTRACT

The present disclosure relates to silica particles comprising repeating units of (SiO$_{4/2}$) that are spherical in shape, which has the benefit of compatibility with personal care components and the resulting personal care applications. The present disclosure also relates to methods of preparing silica particles.

21 Claims, 3 Drawing Sheets

METHOD FOR PRODUCING SILICA PARTICLES AND THEIR USE IN COSMETIC COMPOSITIONS

FIELD

The present disclosure relates to silica particles comprising repeating units of $(SiO_{4/2})$ that have a D90/D10 particle size distribution of about 1.3 or less as measured by laser diffraction and are spherical with a sphericity of 0.9 or more as defined by minor axis/major axis. The present disclosure also relates to personal care compositions comprising such silica particles.

BACKGROUND

The personal care industry thrives on being able to deliver multiple performance products based on mixtures of several components, with each having performance characteristics important to or desirable in the final formulation. Spherical silica fine particles are commonly added in a variety of personal care formulations to enhance their aesthetics with respect to spreadibilty and sensory. However, traditional spherical silica fine particles are inferior in adhesion to the skin.

Spherical silica fine particles have been previously proposed to be incorporated into personal care formulations; however, since the particle diameters of the spherical particles are not uniform, they are not satisfactory in terms of spreadability and sensory. Thus, there is a need to provide a personal care formulation that has excellent spreadability, feel and good adhesion to the skin, less makeup collapse, reduced soft focus effect of making uneven skin tone, and uneven skin texture such as pore and wrinkles less noticeable.

SUMMARY

In a first aspect, the disclosure relates to silica particles comprising repeating units of $(SiO_{4/2})$, wherein the silica particles have a particle size distribution, as defined as D90/D10, of about 1.3 or less as measured by particle size analyzer utilizing laser diffraction, wherein the silica particles are spherical and have a sphericity of 0.9 or more, as defined by minor axis/major axis.

In an aspect, the silica particles have a median particle size (D50) of about 0.5 μm to about 50 μm.

In an aspect, the silica particles have a BET surface area of about 0.1 m$^2$/g to about 100 m$^2$/g.

In an aspect, the silica particles have sphericity of 0.95 or more.

In an aspect, the silica particles are non-porous.

In an aspect, the silica particles are surface-treated with at least one hydrophobicity-imparting agent. In a further aspect, the hydrophobicity-imparting agent is trialkoxysilane compound. In another aspect, the hydrophobicity-imparting agent is hexamethyldisilazane.

In an additional aspect, the disclosure provides a method of making silica particles, the method comprises heating polymethylsilsesquioxane fine particles at a temperature of 500° C. or less to form the silica particles, wherein the silica particles are spherical and have a sphericity of 0.9 or more, as defined by minor axis/major axis.

In an aspect, the polymethylsilsesquioxane fine particles are heated in an atmosphere comprising about 20% oxygen or less.

In an aspect, the polymethylsilsesquioxane fine particles are heated for about 10 minutes to about 6 hours.

In an aspect, the method further comprises reducing the temperature of the polymethylsilsesquioxane fine particles to about 400° C.

In an aspect, the polymethylsilsesquioxane fine particles are heated in an atmosphere comprising about 20% oxygen or less.

In an aspect, the polymethylsilsesquioxane fine particles are heated in an electric furnace, a gas furnace, a far infrared furnace, a medium infrared furnace, or a near infrared furnace.

In another aspect, the disclosure relates to silica particles prepared by the methods disclosed herein. In a further aspect, the silica particles have a median (D50) particle size of about 0.5 μm to about 50 μm as measured by particle size analyzer utilizing laser diffraction particle size analysis.

In an aspect, the silica particles have a particle size distribution defined as D90/D10 of about 1.3 or less as measured by particle size analyzer utilizing laser diffraction particle size analysis.

In an aspect, the silica particles are spherical in shape with sphericity higher than 0.9.

In an aspect, the silica particles are non-porous.

In an aspect, a personal care formulation comprises the silica particles as described herein. In some aspects, the composition further comprises a preservative, an antioxidant, a binder, an anti-foam agent, an anti-static agent, a colorant, an emulsion stabilizer, an oxidation agent, a propellant, an opacity agent, a UV-filter, a UV-absorber, a denaturing agent, a viscosity regulator, a denaturing agent, a chelating agent, a gum or thickener, an oil, a wax, a fragrance, an essential oil, an emulsifier, a surfactant, and combinations thereof. In a further aspect, the personal care is a deodorant, an antiperspirant, a skin cream, a facial cream, a hair shampoo, a hair conditioner, a mousse, a hair styling gel, a hair spray, a protective cream, a lipstick, a facial foundations, blushes, makeup, and mascara, a skin care lotion, a moisturizer, a facial treatment, a personal cleanser, a facial cleanser, a bath oil, a perfume, a shaving cream, a pre-shave lotion, an aftershave lotion, a cologne, a sachet, a toothpaste, or a sunscreen.

DETAILED DESCRIPTION

I. Definitions

Unless otherwise indicated, any atom with unsatisfied valences is assumed to have hydrogen atoms sufficient to satisfy the valences.

The singular forms "a," "an," and "the" include plural referents unless the context dictates otherwise.

Furthermore, "and/or", where used herein, is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The phrase "BET surface area", as used herein, refers to Brunauer-Emmett-Teller surface area.

Figure 2:
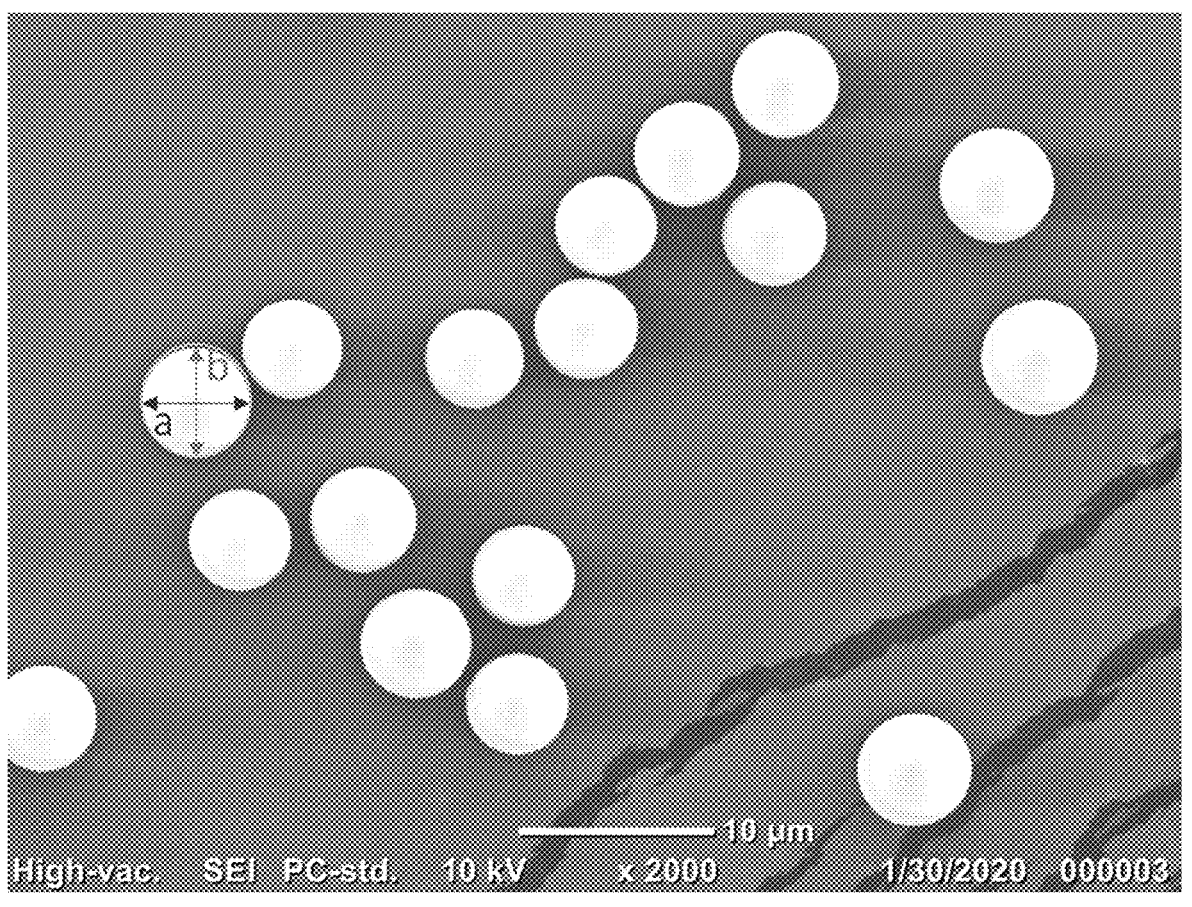
FIG. 2 is an image showing determination of sphericity of particle (minor axis/major axis).

The term "sphericity", as used herein, refers to a parameter to indicate how closely the particle resembles to a perfect sphere and is defined as major axis/minor axisminor axis/major axis obtained from Scanning Microscope Images of the particles. (See FIG. 2)

As used herein, the following definitions shall apply unless otherwise indicated. For purposes of the present disclosure, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 6th Ed., Smith, M. B. and March, J., eds. John Wiley & Sons, New York: 2007, the entire contents of which are hereby incorporated by reference.

Various aspect of the disclosure are described in greater detail below.

II. Silica Particles

In one aspect, the present disclosure is directed to silica particles comprising units of $(SiO_{4/2})$, wherein the silica particles have a D90/D10 particle size distribution of about 1.3 or less as measured by particle size analyzer utilizing laser diffraction particle size analysis, wherein the silica particles are spherical and have a sphericity of 0.9 or more, as defined by minor axis/major axis.

a. Particle Size

In some aspects, the silica particles have a D90/D10 particle size distribution of about 1.0 to about 1.2. In some aspects, the silica particles have a D90/D10 particle size distribution of about 1.0, about 1.1, or about 1.2.

In some aspects, the silica particles have a median (D50) particle size of about 0.5 μm to about 50 μm. In a further aspect, the the silica particles have a median (D50) particle size of about 1 μm to about 20 μm. In another aspect, the the silica particles have a median (D50) particle size of about 1 μm to about 10 μm. In yet another aspect, the the silica particles have a median (D50) particle size of about 1 μm to about 5 μm. In some aspects, the silica particles have a median (D50) particle size of about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 10, about 15, about 20, about 25, about 30, about 35, about 40, about 45, or about 50 μm.

b. Surface Area

In some aspects, the silica particles have a BET surface area of about 0.1 $m^2/g$ to about 100 $m^2/g$ as measured by TriStar II Plus (Micromeritics). In a further aspect, the silica particles have a BET surface area of about 0.1 $m^2/g$ to about 90 $m^2/g$. In some aspects, the silica particles have a BET surface area of about 0.1, about 0.25, about 0.5, about 0.75, about 1, about 1.5, about 2, about 2.5, about 3, about 3.5, about 4, about 4.5, about 5, about 10, about 15, about 20, about 25, about 30, about 35, about 40, about 45, about 50, about 55, about 60, about 65, about 70, about 75, about 80, about 85, about 90, about 95, or about 100 $m^2/g$.

c. Particle Sphericity

In some aspects, the silica particles have sphericity of 0.95 or more. In some aspects, the silica particles have a sphericity of 0.95 to 1.

d. Particle Surface

In some aspects, the silica particles are non-porous.

In some aspects, the silica particles are surface-treated with at least one hydrophobicity-imparting agent. In some aspects, the hydrophobicity-imparting agent is an alkylsilane, (e.g., triethoxycaprylyl silane or dimethylsilyl agent), a metal soap (e.g., isopropyl titanium triisostearate), a stearyl modified amino acid (e.g., disodium stearoyl glutamate and aluminium hydroxide), a silicone (e.g., dimethicone), fluorinated (e.g., perfluorooctyl triethoxysilane), and mixtures thereof. In some aspects, the hydrophobicity-imparting agent is hexamethyldisilazane.

III. Methods

In an aspect, the present disclosure is directed to a method of making silica particles, the method comprises heating polymethylsilsesquioxane fine particles at a temperature of 600° C. or less to form the silica particles, wherein the silica particles are spherical and have a sphericity of 0.9 or more, as defined by minor axis/major axis.

i. Temperature

In some aspects, the polymethylsilsesquioxane fine particles are heated at a temperature of about 500° C. or less. In a further aspect, the polymethylsilsesquioxane fine particles are heated at a temperature or about 400° C. or less.

In some aspects, the polymethylsilsesquioxane fine particles are heated in an electric furnace, a gas furnace, a far infrared furnace, a medium infrared furnace, or a near infrared furnace.

ii. Atmosphere

In some aspects, the polymethylsilsesquioxane fine particles are heated in an atmosphere comprising about 20% oxygen or less. In a further aspect, the polymethylsilsesquioxane fine particles are heated in an atmosphere comprising about 15% oxygen or less. In still a further aspect, the polymethylsilsesquioxane fine particles are heated in an atmosphere comprising about 10% oxygen or less. In some aspects, the polymethylsilsesquioxane fine particles are heated in an atmosphere comprising about 20% or less, about 15% or less, about 10% or less, or about 5% oxygen or less. In some aspects, the polymethylsilsesquioxane fine particles are heated in an atmosphere comprising about 20%, about 15%, about 10%, about 5%, about 4%, about 3%, about 2%, or about 1% oxygen.

iii. Time

In some aspects, the polymethylsilsesquioxane fine particles are heated for about 10 minutes to about 6 hours. In a further aspect, the polymethylsilsesquioxane fine particles are heated for about 30 minutes to about 5 hours. In some aspects, the polymethylsilsesquioxane fine particles are heated for about 10 minutes, about 15 minutes, about 20 minutes, about 25 minutes, about 30 minutes, about 35 minutes, about 40 minutes, about 45 minutes, about 50 minutes, about 55 minutes, about 1 hour, about 1.25 hours, about 1.5 hours, about 1.75 hours, about 2 hours, about 2.25 hours, about 2.5 hours, about 2.75 hours, about 3 hours, about 2.25 hours, about 3.5 hours, about 3.75 hours, about 4 hours, about 4.25 hours, about 4.5 hours, about 4.75 hours, about 5 hours, about 5.25 hours, about 5.5 hours, about 5.75 hours, or about 6 hours.

b. Optional Heating Step

In some aspects, the method may further comprise reducing the temperature of the polymethylsilsesquioxane fine particles to about 400° C.

i. Atmosphere

In some aspects, the polymethylsilsesquioxane fine particles are heated in an atmosphere comprising about 20% oxygen or less. In a further aspect, the polymethylsilsesquioxane fine particles are heated in an atmosphere comprising about 15% oxygen or less. In still a further aspect, the polymethylsilsesquioxane fine particles are heated in an atmosphere comprising about 10% oxygen or less. In some aspects, the polymethylsilsesquioxane fine particles are heated in an atmosphere comprising about 20% or less, about 15% or less, about 10% or less, or about 5% oxygen or less. In some aspects, the polymethylsilsesquioxane fine particles are heated in an atmosphere comprising about 20%, about 15%, about 10%, about 5%, about 4%, about 3%, about 2%, or about 1% oxygen.

ii. Time

In some aspects, the polymethylsilsesquioxane fine particles are heated for about 10 minutes to about 1 hour. In a further aspect, the polymethylsilsesquioxane fine particles are heated for about 45 minutes. In some aspects, the polymethylsilsesquioxane fine particles are heated for about 10 minutes, about 15 minutes, about 20 minutes, about 25 minutes, about 30 minutes, about 35 minutes, about 40 minutes, about 45 minutes, about 50 minutes, about 55 minutes, or about 1 hour.

c. Properties

In an aspect, the silica particles prepared by the method, described herein, have a median (D50) particle size of about 0.5 μm to about 50 μm as measured by laser diffraction.

i. Particle Size

In some aspects, the silica particles have a median (D50) particle size of about 0.5 μm to about 50 μm. In a further aspect, the the silica particles have a median (D50) particle size of about 1 μm to about 20 μm. In another aspect, the the silica particles have a median (D50) particle size of about 1 μm to about 10 μm. In yet another aspect, the the silica particles have a median (D50) particle size of about 1 μm to about 5 μm. In some aspects, the silica particles have a median (D50) particle size of about 0.5, about 0.75, about 1, about 1.25, about 1.5, about 1.75, about 2, about 2.25, about 2.5, about 2.75, about 3, about 3.25, about 3.5, about 3.75, about 4, about 4.25, about 4.5, about 4.75, about 5, about 10, about 15, about 20, about 25, about 30, about 35, about 40, about 45, or about 50 μm.

In some aspects, the the silica particles have a D90/D10 particle size distribution of about 1.3 or less as measured by laser diffraction. In some aspects, the silica particles have a D90/D10 particle size distribution of about 1.0, about 1.1, about 1.2, or about 1.3.

ii. Particle Sphericity

In some aspects, the silica particles are spherical in shape with sphericity higher than 0.9. In some aspects, the silica particles are spherical in shape with sphericity of 0.9 to 1.

iii. Particle Surface

In some aspects, the silica particles are non-porous.

In some aspects, the silica particles are surface-treated with at least one hydrophobicity-imparting agent. In some aspects, the hydrophobicity-imparting agent is an alkylsilane, (e.g., triethoxycaprylyl silane or dimethylsilyl agent), a metal soap (e.g., isopropyl titanium triisostearate), a stearyl modified amino acid (e.g., disodium stearoyl glutamate and aluminium hydroxide), a silicone (e.g., dimethicone), fluorinated (e.g., perfluorooctyl triethoxysilane), and mixtures thereof. In some aspects, the hydrophobicity-imparting agent is hexamethyldisilazane.

IV. Personal Care

In an additional aspect of the present disclosure, the products of the present disclosure, i.e., the silica particles, may be formulated into a personal care item.

In some aspects, the personal care item may be a cosmetic or a medical product.

In an aspect, the personal care composition further comprises a preservative, an antioxidant, a binder, an anti-foam agent, an anti-static agent, a colorant, an emulsion stabilizer, an oxidation agent, a propellant, an opacity agent, a UV-filter, a UV-absorber, a denaturing agent, a viscosity regulator, a denaturing agent, a chelating agent, a gum or thickener, an oil, a wax, a fragrance, an essential oil, an emulsifier, a surfactant, and combinations thereof.

In some aspects, the personal care composition may be formulated with a preservative, an antioxidant, a chelating agent, a gum or thickener, an oil, a wax, a fragrance, an essential oil, an emulsifier, a surfactant, and combinations thereof.

In some aspects, the products of the present disclosure may be added to formulations comprising make-ups, color cosmetics, foundations, blushes, lipsticks, lip balms, eyeliners, mascaras, oil removers, color cosmetic removers, and powders.

In some aspects, the products of present disclosure are blended with a hydrophobizing powder. The hydrophobizing powder may be obtained by hydrophobizing the surface of one or more organic or inorganic powders. In some aspects, the one or more organic or inorganic powder may include, without limit, silicone resin particles, nylon-12, PMMA, cellulose, modified starch, talc, boron nitride, polyurethane, and kaolin particles.

The personal care composition can be a personal care application including deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products (e.g., nail polish, nail polish remover, nail creams and lotions, cuticle softeners), protective creams (e.g., sunscreen, insect repellent and anti-aging products), color cosmetics (e.g., lipsticks, foundations, face powders, eye liners, eye shadows, blushes, makeup, and mascaras), and dental care (e.g., toothpaste). The personal care application can also be a drug delivery system for topical application of a medicinal composition that can be applied to the skin.

In one aspect, the personal care composition further comprises one or more personal care ingredients. Suitable personal care ingredients include, without limit, emollients, moisturizers, humectants, pigments (e.g., pearlescent pigments such as bismuth oxychloride and titanium dioxide coated mica), colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents (e.g., fumed silica or hydrated silica), particulate fillers (e.g., talc, kaolin, starch, modified starch, mica, nylon, clays, such as, for example, bentonite and organo-modified clays).

In some aspects, the one or more personal care components included in the personal care compositions are selected from the group consisting of a humectant, emollient, moisturizer, pigment, colorant, fragrance, biocide, preservative, antioxidant, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, and thickening agent. In some aspects, the one or more emollients is selected from the group consisting of triglyceride esters, wax esters, alkyl or alkenyl ester of fatty acids, polyhydric alcohol esters, and mixtures thereof. In some aspects, the one or more personal care components is a silicone oil, an organic oil, or mixtures thereof.

In one aspect, the personal care composition is an antiperspirant composition that comprises a polymer composition or product described herein and one or more active antiperspirant agents. Suitable antiperspirant agents include, but are not limited to, the Category I active antiperspirant ingredients listed in the U.S. Food and Drug Administration's Oct. 10, 1993 Monograph on antiperspirant drug products for over-the-counter human use including aluminum halides, aluminum hydroxyhalides, for example, aluminum chlorohydrate, and complexes or mixtures thereof with zirconyl oxyhalides and zirconyl hydroxyhalides, (e.g., aluminum-zirconium chlorohydrate, and aluminum zirconium glycine complexes, such as aluminum zirconium tetrachlorohydrex gly).

In another aspect, the personal care composition is a skin care composition comprising a polymer composition or product described herein, and a vehicle, such as a silicone oil or an organic oil. The skin care composition can also include emollients, such as triglyceride esters, wax esters, alkyl or alkenyl esters of fatty acids or polyhydric alcohol esters, pigments, vitamins (e.g., Vitamin A, Vitamin C, and Vitamin E), sunscreen or sunblock compounds (e.g., titanium dioxide, zinc oxide, oxybenzone, octylmethoxy cinnamate, butylmethoxy dibenzoylm ethane, p-aminobenzoic acid, and octyl dimethyl-p-aminobenzoic acid).

In yet another aspect, the personal care composition is a color cosmetic composition such as a lipstick, a makeup or mascara. The color cosmetic composition comprises a polymer composition or product described herein and a coloring agent (e.g., pigment, water-soluble dye, or liposoluble dye).

EXAMPLES

The following examples are included to demonstrate various aspects of the present disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific examples which are disclosed and still obtain a like or similar result without departing from the spirit and scope of the disclosure.

Example 1: Preparation of Spherical Particles (A)

In a suitable vessel, width×depth×height of 415×415×50 mm, 500 g of polymethylsilsesquioxane fine particles (Momentive TOSPEARL 145A) with an average particle size of 4.5 m were added and heated at 500° C. for 30 minutes in an atmosphere of 10% oxygen concentration in nitrogen mixed air. The particles were then heated at 400° C. for 45 minutes in an air atmosphere. 445 g of spherical silica fine particles (A) were obtained. The median (D50) particle size of the obtained spherical silica fine particles was 3.8 μm, the particle size dispersion D90/D10 was 1.11 and the BET specific surface area was 1.32 m$^2$/g as measured by TriStar II Plus (Micromeritics, Norcross, GA).

Example 2: Preparation of Spherical Particles (B)

In a suitable vessel, width×depth×height 415×415×50 mm, 500 g of polymethylsilsesquioxane fine particles (Momentive TOSPEARL 120A) with an average particle diameter of 2 m were added and heated at 450° C. in an air atmosphere for 5 hours. 448 g of spherical silica fine particles (B) were obtained. The median (D50) particle size of the obtained spherical silica fine particles was 1.7 μm, the particle size dispersion D90/D10 was 1.17, and the specific surface area was 2.7 m$^2$/g as measured by TriStar II Plus.

Example 3: Preparation of Spherical Particles (C)

In a suitable vessel, width×depth×height of 415×415×50 mm, 300 g of polymethylsilsesquioxane fine particles (Momentive TOSPEARL 1110A) with an average particle size of 11 m were added and heated at 500° C. for 30 minutes, under 10% oxygen concentration in nitrogen mixed air atmosphere. The particles were then heated at 400° C. for 45 minutes in an air atmosphere. 267 g of spherical silica fine particles (C) was obtained. The median (D50) particle size of the obtained spherical silica fine particles was 9.4 μm, the particle size dispersion D90/D10 was 1.08, and the specific surface area was 0.6 m$^2$/g as measured by Tri Star II Plus.

Example 4: Preparation of Surface-Treated Spherical Particles (D)

In a suitable vessel, 20 gm of spherical silica particles (A) were dispersed in 10 gms of water. The mixture was mixed with overhead stirrer (IKA Eurostar 100 digital overhead stirrer). Then, 6 gms of hexamethyldisilazane was added to the mixture and the mixture was stirred at 25° C. for 6 hrs. The slurry was then dried at 150° C. for 3 hrs. The dried powder was then sieved through 50 micron sieve. The resulted spherical powder (D) had median particle size (D50) about 3.8 micron. The particle size distribution measured as D90/D10 was 1.11.

Example 5: Powder Foundation

Powder foundations were prepared with the composition shown in Table 1 using the above silica fine particles (A) to (C) and Tospearl fine particles and Silica fine particles. In the preparation method, first, ingredients of Phase A and Phase B were mixed in Hanil Lab Mixer, then add premixed ingredients of Phase C, and again mixed uniformly using Hanil Lab Mixer, finally the mixture was compression molded into a metal plate.

TABLE 1

Powder Foundation Formulation

| Phase | | Example | | | Comparative Example | | | |
|---|---|---|---|---|---|---|---|---|
| | | 1 | 2 | 3 | 1 | 2 | 3 | 4 |
| A | Spherical silica particles (A) | 10 | — | — | — | — | — | — |
| | Spherical silica particles (B) | — | 10 | — | — | — | — | — |
| | Spherical silica particles (C) | — | — | 10 | — | — | — | — |
| | 4.5 μm Spherical Methylsilsesquioxane particles, D90/D10: 1.11, specific surface area 67 m$^2$/g | — | — | — | 10 | — | — | — |
| | 5 μm Spherical silica particles, D90/D10: specific surface area 800 m$^2$/g | — | — | — | — | 10 | — | — |
| | 3 μm Spherical silica particles, D90/D10: specific surface area 40 mm$^2$/g | — | — | — | — | — | 10 | — |
| | Polymethylhydrosiloxane treated Talc | 22 | 22 | 22 | 22 | 22 | 22 | 27 |
| | Polymethylhydrosiloxane treated Mica | 33 | 33 | 33 | 33 | 33 | 33 | 38 |
| | Polymethylhydrosiloxane treated Titanium Dioxide | 11.5 | 11.5 | 11.5 | 11.5 | 11.5 | 11.5 | 11.5 |
| | Polymethylhydrosiloxane treated Zinc Oxide | 3 | 3 | 3 | 3 | 3 | 3 | 3 |
| | Boron Nitride Powder | 4 | 4 | 4 | 4 | 4 | 4 | 4 |
| | Microsphere-M-305 (Polymethylmethacrylate Particles) (Matsumoto Yushi-Seiyaku Co. Ltd) | 1 | 1 | 1 | 1 | 1 | 1 | 1 |
| | Magnesium Stearate | 2 | 2 | 2 | 2 | 2 | 2 | 2 |
| B | Polymethylhydrosiloxane treated Iron Oxides (CI 77492) | 2.2 | 2.2 | 2.2 | 2.2 | 2.2 | 2.2 | 2.2 |
| | Polymethylhydrosiloxane treated Iron Oxides (CI 77491) | 0.54 | 0.54 | 0.54 | 0.54 | 0.54 | 0.54 | 0.54 |
| | Polymethylhydrosiloxane treated Iron Oxides (CI 77499) | 0.36 | 0.36 | 0.36 | 0.36 | 0.36 | 0.36 | 0.36 |
| C | Polydimethylsiloxane trimethylsiloxysilicate (Momentive SS4267) | 2 | 2 | 2 | 2 | 2 | 2 | 2 |
| | Pentylene Glycol | 2 | 2 | 2 | 2 | 2 | 2 | 2 |
| | Silsoft B 3820 (Momentive) (Isododecane, Dimethicone) | 1 | 1 | 1 | 1 | 1 | 1 | 1 |
| | Caprylic/Capric Triglyceride | 1.6 | 1.6 | 1.6 | 1.6 | 1.6 | 1.6 | 1.6 |
| | Sorbitan Sesquiisostearate | 0.5 | 0.5 | 0.5 | 0.5 | 0.5 | 0.5 | 0.5 |
| | Diisostearyl Malate | 0.5 | 0.5 | 0.5 | 0.5 | 0.5 | 0.5 | 0.5 |
| | Ethylhexyl Methoxycinnamate | 2 | 2 | 2 | 2 | 2 | 2 | 2 |
| | Tocopheryl Acetate | 0.5 | 0.5 | 0.5 | 0.5 | 0.5 | 0.5 | 0.5 |
| | Phenoxyethanol | 0.3 | 0.3 | 0.3 | 0.3 | 0.3 | 0.3 | 0.3 |

The evaluation results of "Spreadability", "Skin Smoothness", "Skin Compatibility", "Soft Focus effect", and "longlasting makeup wearing after 12 hours" are also shown in Table 2 together with the composition. The evaluation was made by 10 panelists who scored each item according to the following criteria and evaluated by the average value.

"Very good": 5 points; "Good": 4 points; "Normal": 3 points; "Slightly defective": 2 points; and "Bad": 1 point.

TABLE 2

Evaluation Results

| | | Example | | | Comparative Example | | | |
|---|---|---|---|---|---|---|---|---|
| | | 1 | 2 | 3 | 1 | 2 | 3 | 4 |
| Evaluation Results | Spreadability during application | 4.6 | 4.2 | 4.8 | 4.8 | 3.7 | 3.6 | 4.6 |
| | Smoothness during application | 4.7 | 4.8 | 4.8 | 4.4 | 3.8 | 4.2 | 4.2 |

TABLE 2-continued

Evaluation Results

| | Example | | | Comparative Example | | | |
|---|---|---|---|---|---|---|---|
| | 1 | 2 | 3 | 1 | 2 | 3 | 4 |
| Compatiblity to skin | 4.7 | 4.7 | 4.5 | 3.9 | 4.2 | 4.1 | 3.9 |
| Soft focus effect | 4.5 | 4.8 | 4.1 | 3.8 | 4.2 | 4.6 | 4.3 |
| Skin moisturized feel | 4.5 | 4.5 | 4.6 | 3.9 | 2.7 | 4.3 | 3.8 |
| Makeup lasting after 12 hours | 4.5 | 4.7 | 4.2 | 3.0 | 2.7 | 4.2 | 3.5 |

Example 6: Powder Formulations

Powder formulations were prepared with the composition shown below in Table 3 using the above silica fine particles of Example 1 (A) and comparative spherical silica (Sunsphere NP-30, Asahi Glass SI-Tech. Co. Ltd.) with 4 micron mean particle size and with D90/D1=2.7. The ingredients were mixed in a 100 gm speedmixer container and the powders were mixed for 5 minutes to obtain a uniformly mixed loose powder formulation.

The friction coefficient of the powder formulation were measured with CSM Tribometer. The powder was rubbed on leather (2 mg/cm$^2$) for 10 s. The friction was measured with 1 cm stainless steel diameter probe with leather (Testfabrics Inc.) attached to the flat surface. The friction was measured at 1 cm/s speed for probe reciprocating 2 cm back in forth for 10 cycles. The friction coefficient was reported as average friction coefficient for 10 cycles.

TABLE 3

Powder Formulations

| Ingredient | International Nomenclature Cosmetic Ingredient (INCI) | Example 5.1 | Comp. Ex. 5.2 |
|---|---|---|---|
| Talc U-11S2 | Talc (and) Triethoxycaprylylsilane | 23.4 | 23.4 |
| GMS-11S2 | Mica (and) Triethoxycaprylylsilane | 35.1 | 35.1 |
| JTTO-MS7 (Kobo) | Titanium Dioxide (and) Alumina (and) Methicone | 12.2 | 12.2 |
| Zano Plus | Zinc Oxide (and) Triethoxycaprylylsilane | 3.2 | 3.2 |
| Softouch CC60586058 | Boron Nitride | 4.3 | 4.3 |
| BYO-12 | CI 77492 (and) Isopropyl Titanium Triisostearate | 2.3 | 2.3 |
| BRO-12 | CI 77491 (and) Isopropyl Titanium Triisostearate | 0.6 | 0.6 |
| BBO-12 | CI 77499 (and) Isopropyl Titanium Triisostearate | 0.4 | 0.4 |
| SS4267 | Dimethicone (and) Trimethylsiloxysilicate | 2.1 | 2.1 |
| CCTG | Caprylic/Capric Triglyceride | 2.8 | 2.8 |
| Cosmol 182 V | Sorbitan Sesquiisostearate | 0.5 | 0.5 |
| Cosmol 222 | Diisostearyl Malate | 0.5 | 0.5 |
| Phenoxyethanol | Phenoxyethanol | 0.3 | 0.3 |
| OMC | Ethylhexyl Methoxy cinnamate | 2.1 | 2.1 |
| Example 1 (A) | D50 = 3.8 micron, D50/D10 = 1.11 | 10.0 | — |
| Comparable silica | D50 = 4 micron, D50/D10 = 2.7 | — | 10.0 |

Figure 1:
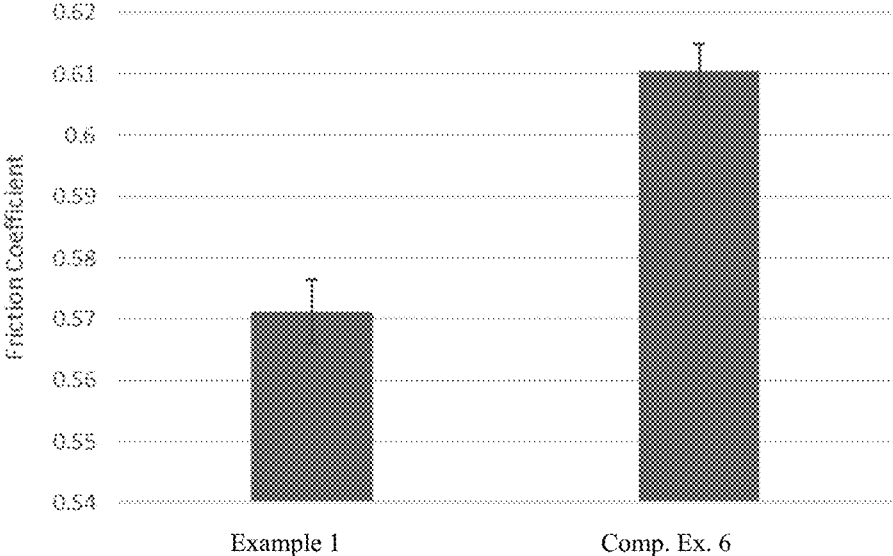
FIG. 1 is a graph showing the powder formulation with silica with narrow particle size distribution (D90/D10=1.1) showed lower friction coefficient than the formulation with higher particle size distribution (D90/D10=1.9).
Figure 3A:
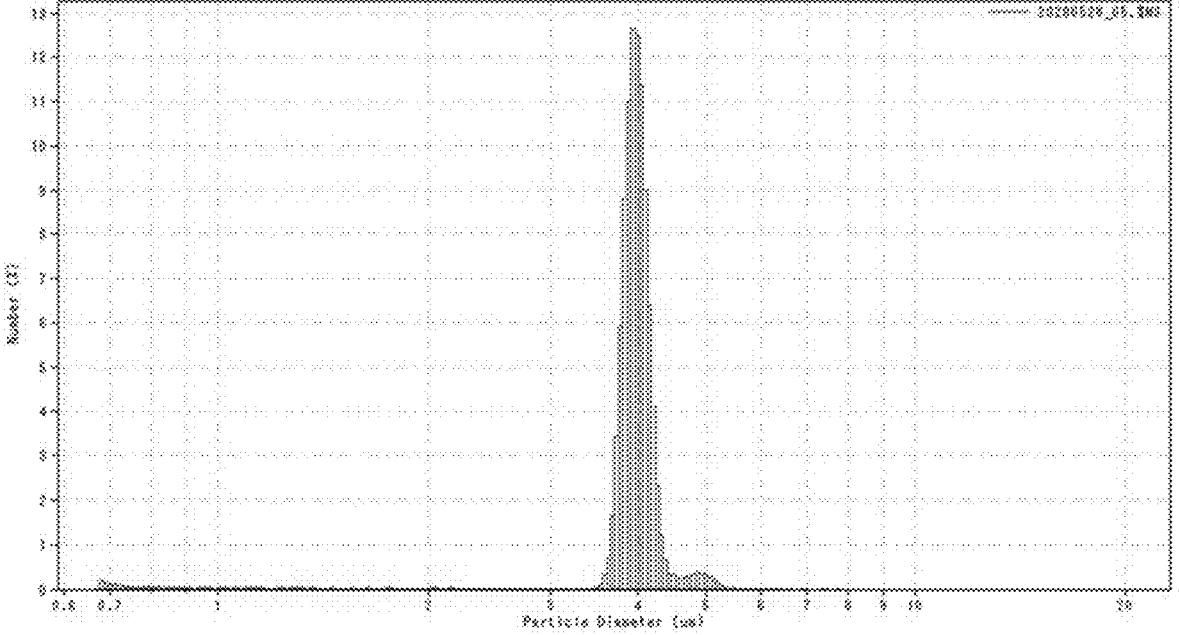
FIG. 3A and FIG. 3B are distribution graphs showing particle size distribution of spherical particles as prepared using the method of Example 1 (FIG. 3A) and Comparative Example 6 (FIG. 3B).
Figure 3B:
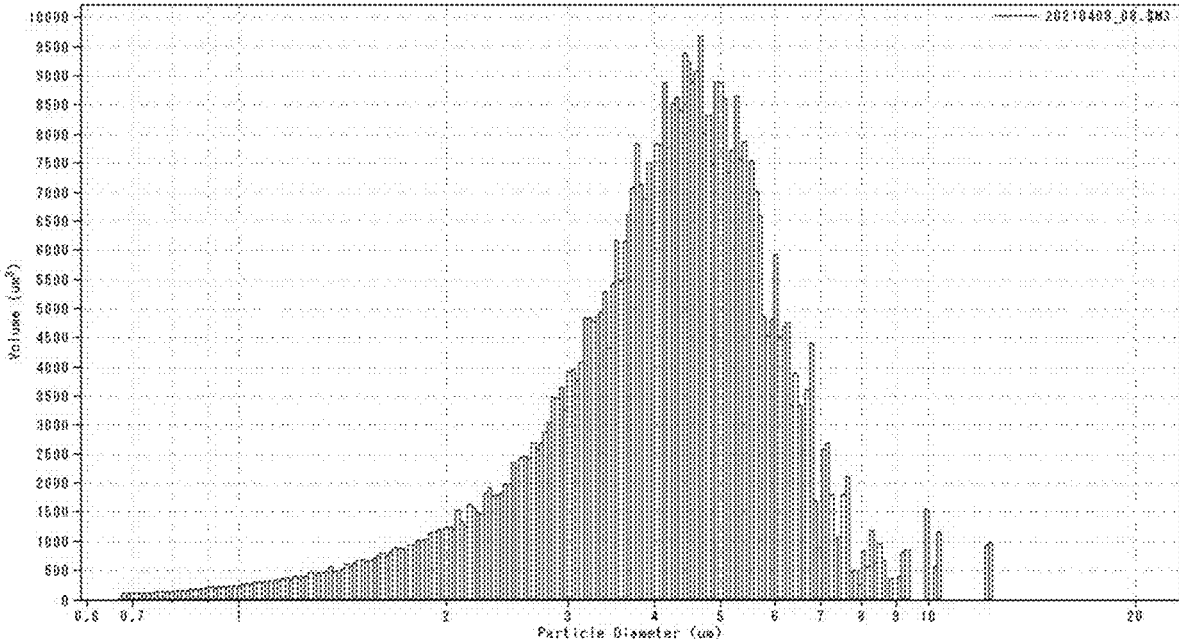

FIG. 1 shows the powder formulation with silica with narrow particle size distribution (D90/D10=1.1) showed lower friction coefficient than the formulation with higher particle size distribution (D90/D10=2.7). FIG. 3A and FIG. 3B shows the particle size distribution of spherical particles of Example 1 (D90/D10=1.1, D50=3.9 μm) and comparative silica (D90/D10=2.70, D50=4.3 μm).

Example 7: Emulsified Foundation

Using the above silica fine particles (A), an emulsified foundation having the composition shown below was prepared. The preparation method was as follows: First, ingredients (5) to (8) were mixed with a Henschel mixer, then ingredients (1) and (3) to (4) were added thereto, and the mixture was thoroughly mixed, and then pulverized and classified. Further, ingredients (2) and (9) to (18) were added, treated with a homomixer, deaerated, and filled in a container.

TABLE 4

Emulsified Foundation Formulation

| | Ingredient | Amount (wt. %) |
|---|---|---|
| 1 | Silica fine particles (A) | 10.0 |
| 2 | Dimethyl silicone (viscosity 10 mPa · s) | 7.0 |
| 3 | Titanium oxide | 5.0 |
| 4 | Anhydrous silicic acid | 3.0 |
| 5 | Talc | 8.0 |
| 6 | Bengala | 1.0 |
| 7 | Black iron oxide | 0.5 |
| 8 | Yellow iron oxide | 1.0 |
| 9 | Octamethylcyclotetrasiloxane | 10.0 |
| 10 | Rosin pentaerislit ester | 2.0 |
| 11 | Neopentyl glycol diisooctanoate | 4.0 |
| 12 | Squalene | 2.5 |
| 13 | Glycerin triisooctanoate | 2.0 |
| 14 | Purified water | 35.0 |
| 15 | 1,3-butylene glycol | 4.0 |
| 16 | Ethanol | 8.0 |
| 17 | Preservatives | 0.1 |
| 18 | Fragrance | Balance |

Example 8: Powder Foundation

Using the above silica fine particles (A), a dual-purpose powder foundation having the composition shown below was prepared. In the preparation method, first, ingredients (1) and (3) to (10) were mixed and pulverized, transferred to a Henschel mixer, and then ingredients (2) and (11) to (16) were added and mixed uniformly. Then the mixture was compression molded into a metal plate.

TABLE 5

Powder Foundation Formulation

| | Ingredient | Amount (wt. %) |
|---|---|---|
| 1 | Silica fine particles (A) | 15.0 |
| 2 | Dimethyl silicone (viscosity 10 mPa · s) | 5.0 |
| 3 | Mica | 5.0 |
| 4 | Talc | 5.0 |
| 5 | Titanium oxide | 15.0 |
| 6 | Mica Titanium | 3.5 |
| 7 | Iron oxide (red, yellow, black) | 7.0 |
| 8 | Zinc oxide | 4.0 |
| 9 | Aluminum oxide | 10.0 |
| 10 | Barium sulfate | 5.0 |
| 11 | Lanolin | 5.0 |
| 12 | Vaseline | 1.5 |
| 13 | Liquid paraffin | 1.0 |
| 14 | Isopropyl millistate | 1.5 |
| 15 | Preservatives | Balance |
| 16 | Fragrance | Balance |

Example 9: Powder Eyeshadow

Using the above silicone particles (A), a powder eyeshadow with the composition shown below was prepared. The preparation method was as follows: First, ingredients (1) and (3) to (10) were mixed and crushed, transferred to a Henschel mixer, then ingredients (2) and (11) were added and mixed uniformly, then the mixture was compression molded into a metal plate.

TABLE 6

Powder Eyeshadow Formulation

| | Ingredient | Amount (wt. %) |
|---|---|---|
| 1 | Silica fine particles (A) | 20.0 |
| 2 | Dimethyl silicone (viscosity 10 mPa · s) | 5.0 |
| 3 | Mica | Balance |
| 4 | Talc | 15.0 |
| 5 | Mica Titanium | 8.0 |
| 6 | Zinc stearate | 4.0 |
| 7 | Zinc laurate | 4.0 |
| 8 | Yellow iron oxide | 0.7 |
| 9 | Black iron oxide | 0.7 |
| 10 | Red iron oxide | 0.7 |
| 11 | Liquid paraffin | 8.0 |
| 12 | Preservatives and fragrances | Balance |

Example 10: Two-Layer Separation Type Sunscreen

Using the above silicone particles (A), a two-layer separation type sunscreen emulsion having the composition shown below was prepared. In the preparation method, ingredients (1) to (7) were first dispersed and mixed with a disper, and then the aqueous phase ingredients (8) to (11) were added and stirred to emulsify.

TABLE 7

Two-Layer Sunscreen Formulation

| | Ingredient | Amount (wt. %) |
|---|---|---|
| 1 | Silica fine particles (A) | 10.0 |
| 2 | Dimethyl silicone (viscosity 10 mPa · s) | 5.0 |
| 3 | Decamethylcyclopentasiloxane | 20.0 |

TABLE 7-continued

Two-Layer Sunscreen Formulation

| | Ingredient | Amount (wt. %) |
|---|---|---|
| 4 | Polyethter-modified silicone | 1.0 |
| 5 | Squalene | 8.0 |
| 6 | Hydrophobicized titanium oxide | 5.0 |
| 7 | Octyl methoxycinnamic acid | 2.0 |
| 8 | Glycerin | 2.0 |
| 9 | Sodium Chloride | 0.4 |
| 10 | Polysorbate 20 | 0.9 |
| 11 | Ethanol | 12.0 |
| 12 | Fragrance | Balance |
| 13 | Purified water | Balance |

Example 11: Sunscreen Cream

Using the above silicone particles (A), a sunscreen cream having the composition shown below was prepared. In the preparation method, ingredients (1) to (8) were first dispersed and mixed with a disper, and then the aqueous phases ingredients (8) to (10) were added and stirred to emulsify.

TABLE 8

Sunscreen Cream Formulation

| | Ingredient | Amount (wt. %) |
|---|---|---|
| 1 | Silica fine particles (A) | 10.0 |
| 2 | Dimethyl silicone (viscosity 10 mPa · s) | 7.0 |
| 3 | Hydrophobic titanium dioxide | 10.0 |
| 4 | Hydrophobic zinc oxide | 10.0 |
| 5 | Squalene | 15.0 |
| 6 | Glycerin diisostearate | 3.0 |
| 7 | Preservatives | 0.1 |
| 8 | Fragrance | 0.1 |
| 9 | Purified water | Balance |
| 10 | 1,3-butylene glycol | 5.0 |

Example 12: Solid White Powder

Using the above silicone particles (A), a solid white powder having the composition shown below was prepared. Preparation method is as below. First, the ingredients (1) and (3) to (6) were mixed and crushed, transferred to a Henschel mixer, then ingredients (2) and (7) to (10) were added, mixed uniformly, and compression-molded onto a metal plate.

TABLE 9

Solid White Powder Formulation

| | Ingredient | Amount (wt. %) |
|---|---|---|
| 1 | Silica fine particles (A) | 20.0 |
| 2 | Dimethyl silicone (viscosity 10 mPa · s) | 7.0 |
| 3 | Mica Balance | Balance |
| 4 | Talc | 15.0 |
| 5 | Titanium oxide | 1.0 |
| 6 | Yellow iron oxide | 1.0 |
| 7 | Liquid paraffin | 10.0 |
| 8 | Beeswax | 3.0 |
| 9 | Preservatives | Balance |
| 10 | Fragrance | Balance |

Example 13: Blusher

Using the above silica fine particles (A), a blusher having the composition shown below was prepared. The preparation method was as follows: First, the ingredients (1) to (6) were mixed and crushed, transferred to a Henschel mixer, then the ingredients (7) to (10) were added, mixed uniformly, and compression molded into a metal plate.

TABLE 10

Blusher Formulation

| | Ingredient | Amount (wt. %) |
|---|---|---|
| 1 | Silica fine particles (A) | 5.0 |
| 2 | Mica | 10.0 |
| 3 | Titanium oxide | 10.0 |
| 4 | Red iron oxide | 1.5 |
| 5 | Black iron oxide | 1.5 |
| 6 | Yellow iron oxide | 1.5 |
| 7 | Squalene | 7.0 |
| 8 | Dimethyl silicone (viscosity 5 mPa s) | 7.0 |
| 9 | Preservatives | 0.1 |
| 10 | Fragrance | Balance |

Example 14: Lipstick

Using the above silica fine particles (A), a lipstick having the composition shown below was prepared. The preparation method was as follows: ingredients (1)-(11) were heated and melted, then (12) and (13) were added and mixed, the mixture was degassed and poured into a container, rapidly cooled and hardened.

TABLE 11

Lipstick Formulation

| | Ingredient | Amount (wt. %) |
|---|---|---|
| 1 | Silica fine particles (A) | 6.0 |
| 2 | Dimethyl silicone (viscosity 10 mPa · s) | 10.0 |
| 3 | Paraffin wax | 11.0 |
| 4 | Lanolin wax | 12.0 |
| 5 | Candelilla wax | 5.0 |
| 6 | Beeswax | 5.0 |
| 7 | Castor oil | Balance |
| 8 | Glycerin trioctanoate | 2.0 |
| 9 | Titanium oxide | 1.0 |
| 10 | Red No. 201 | 3.0 |
| 11 | Blue No. 1 aluminum lake | 0.5 |
| 12 | Preservatives | Balance |
| 13 | Fragrance | Balance |

Example 15: Skin Primer

Using the above silica fine particles (A), a skin primer having the composition shown below was prepared. The preparation method was as follows: Ingredients (1) to (7) were heated and mixed, ingredients (8) to (13) were separately mixed well, then added to ingredients (1) to (7) and mixed well, finally the aqueous phases ingredients (14) to (18) were added and stirred to emulsify.

TABLE 12

Skin Primer Formulation

| | Ingredients | Amount (wt. %) |
|---|---|---|
| 1 | Dimethicone | 10.5 |
| 2 | Ethylhexyl Methoxycinnamate | 5 |
| 3 | Silica fine particles (A) | 5 |
| 4 | Cylcopentasiloxane (and) Polymethylsilsesquioxane | 4 |
| 5 | Dimethicone, Cetearyl Dimethicone Crosspolymer | 4 |
| 6 | Sorbitan Sesquiisostearate | 0.5 |
| 7 | (Caprylic/Capric) Triglyceride (and) PEG/PPG-20/15 Dimethicone | 4 |
| 8 | Dimethicone | 3 |
| 9 | Hydrogen Dimethicone (and) Zinc Oxide | 1.5 |
| 10 | Hydrogen Dimethicone (and) Titanium Dioxide (and) Aluminum Hydroxide | 1.5 |
| 11 | Methicone (and) Iron Oxide (CI 77492) | 0.05 |
| 12 | Methicone (and) Iron Oxide (CI 77491) | 0.05 |
| 13 | Methicone (and) Iron Oxide (CI 77499) | 0.015 |
| 14 | water | Balance |
| 15 | Glycerin | 5 |
| 16 | Polysorbate 20 | 0.5 |
| 17 | Sodium Chloride | 1 |
| 18 | Phenoxy ethanol | Balance |

Example 16: BB Cream

Using the above silica fine particles (A), a BB cream having the composition shown below was prepared. The preparation method was as follows: Ingredients (1) to (9) were mixed until uniform, ingredients (10) to (15) were separately mixed well, then added to ingredients (1) to (9) and mixed well, then the aqueous phases ingredients (16) to (21) were added and mixed well, finally add (22) and homogenize to uniform.

TABLE 13

BB Cream Formulation

| | Ingredients | Amount (wt. %) |
|---|---|---|
| 1 | Caprylyl Methicone (and) C30-45 Alkyl Cetearyl Dimethicone Crosspolymer | 4 |
| 2 | Dimethicone | 15 |
| 3 | Silica fine particles (A) | 5 |
| 4 | Trifluoropropyldimethylsiloxy/Trimethylsiloxy Silsesquioxane (and) Dimethicone | 2 |
| 5 | (Caprylic/Capric) Triglyceride (and) PEG/PPG-20/15 Dimethicone | 7 |
| 6 | Bisphenylpropyl Dimethicone | 2 |
| 7 | Boron Nitride | 3 |
| 8 | Phenoxyethanol (and) Ethylhexylglycerin | 1 |
| 9 | Fragrance | Balance |
| 10 | Caprylyl Methicone | 5 |
| 11 | Titanium Dioxide (and) Triethoxycaprylylsilane | 2 |
| 12 | Iron Oxide (and) Triethoxycaprylylsilane | 0.5 |
| 13 | Iron Oxide (and) Triethoxycaprylylsilane | 0.2 |
| 14 | Iron Oxide (and) Triethoxycaprylylsilane | 0.05 |
| 15 | Titanium Dioxide (and) Alumina (and) Methicone | 7 |
| 16 | Water | Balance |
| 17 | Trisodium EDTA | 0.2 |
| 18 | Butylene Glycol | 3 |
| 19 | Glycerin | 5 |
| 20 | Sodium Chloride | 1 |
| 21 | Hydroxyphenyl Propamidobenzoic Acid | 1 |
| 22 | Disteardimonium Hectorite | 0.7 |

Example 17: CC Cream

Using the above silica fine particles (A), a CC cream having the composition shown below was prepared. The preparation method was as follows: Ingredients (5) to (14) were mixed until uniform, ingredients (15) to (17) were separately mixed well, then added to ingredients (5) to (14) and mixed well, then the aqueous phases ingredients (1) to (4) were added and mixed well, finally add (18) to (20) and mix to uniform.

TABLE 14

CC Cream Formulation

| | Ingredients | Amount (Wt. %) |
|---|---|---|
| 1 | Water | Balance |
| 2 | Glycerin | 5 |
| 3 | Sodium Chloride | 1 |
| 4 | Propylene Glycol | 8 |
| 5 | PEG-9 Dimethicone | 1 |
| 6 | Caprylic/Capric Triglyceride (and) PEG/PPG-20/15 Dimethicone | 3 |
| 7 | Caprylyl Methicone | 12 |
| 8 | Diphenyl Dimethicone | 5 |
| 9 | Boron Nitride | 1 |
| 10 | Silica fine particles (A) | 5 |
| 11 | Polymethylsilsesquioxane | 1 |
| 12 | Octyl MethoxyCinnamate | 4 |
| 13 | Titanium Dioxide (and) Methylhydrogenpolysiloxane | 5 |
| 14 | Disteardimonium Hectorite | 0.5 |
| 15 | Yellow Iron Oxide (and) Methylhydrogenpolysiloxane | 0.25 |
| 16 | Red Iron Oxide (and) Methylhydrogenpolysiloxane | 0.15 |
| 17 | Black Iron Oxide (and) Methylhydrogenpolysiloxane | 0.08 |
| 18 | Dimethicone/Vinyl Dimethicone Crosspolymer (and) Dimethicone (and) Isohexadecane (and) Cetearyl Methicone | 5 |
| 19 | Fragrance | Balance |
| 20 | Phenoxyethanol (and) Chlorphenesin (and) Glycerin | Balance |

Example 18: Mascara

Using the above silica fine particles (A), a Mascara having the composition shown below was prepared. The preparation method was as follows: Ingredients (3) and (4) were mixed in water then heat to uniform, add ingredients (2) and (5) to (9) and mixed well, heat ingredients (10) to (15) separately, then added to the mixture and mixed well, then cool to 45° C., add ingredients (16) and (17) one by one, and mix to uniform.

TABLE 15

Mascara Formulation

| | Ingredients | Amount (wt. %) |
|---|---|---|
| 1 | Water | Balance |
| 2 | Silica fine particles (A) | 5 |
| 3 | Polyvinylpyrrolidone | 2 |
| 4 | Hydroxyethylcellulose | 1 |
| 5 | Triethanolamine | 1 |
| 6 | Methylparaben | 0.3 |
| 7 | Disodium EDTA | 0.1 |
| 8 | Black Iron Oxide | 10 |
| 9 | Dimethicone PEG-8 Polyacrylate | 7.2 |
| 10 | Stearic Acid | 4.5 |
| 11 | Glyceryl Monostearate | 2 |
| 12 | White Bleached Beeswax | 7 |
| 13 | Carnauba Wax | 4.5 |
| 14 | Hydroxylated Lanolin | 1 |

TABLE 15-continued

Mascara Formulation

| | Ingredients | Amount (wt. %) |
|---|---|---|
| 15 | Propylparaben | Balance |
| 16 | Acrylates Copolymer | 20 |
| 17 | DMDM Hydantoin | Balance |

Example 19: Concealer

Using the above silica fine particles (A), a Concealer having the composition shown below was prepared. The preparation method was as follows: Ingredients (1) and (7) were mixed until uniform and heat to 90° C., add ingredients (8) to (10) and mixed until uniform, pour the mixture into suitable container.

TABLE 16

Concealer Formulation

| | Ingredients | Amount (Wt. %) |
|---|---|---|
| 1 | Boron Nitride | 10 |
| 2 | Silica fine particles (A) | 5 |
| 3 | Dimethicone | Balance |
| 4 | Titanium Dioxide (and) Triethoxycaprylylsilane | 4 |
| 5 | Iron Oxide (and) Triethoxycaprylylsilane | 0.9 |
| 6 | Iron Oxide (and) Triethoxycaprylylsilane | 0.3 |
| 7 | Iron Oxide (and) Triethoxycaprylylsilane | 0.1 |
| 8 | Ozokerite Wax | 5 |
| 9 | Polyethylene | 5 |
| 10 | Synthetic Wax (and) Microcrystalline Wax | 2 |

Example 20: O/W Cream

Using the above silica fine particles (A), an O/W Cream having the composition shown below was prepared. The preparation method was as follows: Ingredients (1) to (3) were mixed and heated to 80° C., ingredients (4) to (6) were mixed separately and added to ingredients (1) to (3), mixed until uniform, cool to room temperature, and add ingredients (7) and (8) and mix until uniform.

TABLE 17

O/W Cream Formulation

| | Ingredients | Amount (Wt. %) |
|---|---|---|
| 1 | Water | Balance |
| 2 | Silica fine particles (A) | 9.5 |
| 3 | Titanium Dioxide, Silica, Aluminum Hydroxide | 0.5 |
| 4 | Polysilicone-34 (and) Isononyl Isononanoate (and) Water | 3 |
| 5 | Dimethicone | 8 |
| 6 | Butyrospermum Parkii (Shea) Butter | 2 |
| 7 | Phenoxyethanol | Balance |
| 8 | Sodium Hyaluronate | 0.1 |

Example 21: W/O Cream

Using the above silica fine particles (A), a WIG Cream having the composition shown below was prepared. The preparation method was as follows: Ingredients (1) to (6) were mixed and heated to 70° C., ingredients (7) to (9) were mixed separately and added to ingredients (1) to (6), mixed to emulsify, and cool to room temperature.

TABLE 18

W/O Cream Formulation

| | Ingredients | Amount (Wt. %) |
|---|---|---|
| 1 | Dimethicone | 1 |
| 2 | Capylyl Methicone | 10 |
| 3 | Silica fine particles (A) | 9 |
| 4 | Hydrogen Dimethicone (and) Titanium Dioxide (and) Aluminum Hydroxide | 1 |
| 5 | (Caprylyl/Capryl) Triglyceride (and) PEG/PPG-20/15 Dimethicone | 3 |
| 6 | Phenoxy ethanol | Balance |
| 7 | water | Balance |
| 8 | Glycerin | 8 |
| 9 | Sodium Chloride | 1 |

Example 22: Eye Cream

Using the above silica fine particles (A), an Eye Cream having the composition shown below was prepared. The preparation method was as follows: Ingredients (1) to (4) were mixed and heated to 70° C., ingredients (5) to (12) were mixed separately and heated to 70° C., then added to ingredients (1) to (4), mixed to emulsify, then cool to 50° C., add ingredient (13) and mix until uniform.

TABLE 19

Eye Cream Formulation

| | Ingredients | Amount (Wt. %) |
|---|---|---|
| 1 | Water | Balance |
| 2 | Silica fine particles (A) | 5 |
| 3 | Glycerin | 3 |
| 4 | Di sodium EDTA | 0.05 |
| 5 | Glyceryl stearate citrate (and) Polyglyceryl-3 stearate (and) Hydrogenated lecithin | 4 |
| 6 | Sodium acrylates copolymer (and) Lecithin | 1 |
| 7 | Cetyl Alcohol | 1.5 |
| 8 | Butyrospermum Parkii (Shea Butter) | 4 |
| 9 | Decyl Isostearate (and) Isostearyl Isostearate | 3 |
| 10 | Argania Spinosa Kernel Oil | 2 |
| 11 | Dimethicone | 3 |
| 12 | Caprylyl Methicone | 3 |
| 13 | Dimethicone/Vinyl Dimethicone Crosspolymer (and) Dimethicone(and) Isohexadecane (and) Cetearyl Methicone | 3 |

Example 23: Skin Serum

Using the above surface treated silica fine particles (D), an Skin Serum having the composition shown below was prepared. The preparation method was as follows: Ingredients (1) to (4) were mixed until uniform, ingredients (5) to (7) were mixed separately and added to ingredients (1) to (4), mixed until uniform, then add ingredients from (8) to (11) one by one, and mix until uniform.

TABLE 20

Skin Serum Formulation

| | Ingredients | Amount (Wt. %) |
|---|---|---|
| 1 | Water | Balance |
| 2 | Silica fine particles (D) | 1 |
| 3 | Alpha-Glucan Oligosaccharide | 0.5 |
| 4 | Hydrolyzed Sodium Hyaluronate | 0.01 |
| 5 | BG | 1 |
| 6 | Pentylene Glycol | 3 |
| 7 | Dipropylene Glycol (and)Polysilicone-29 | 1 |
| 8 | Malus Domestica Fruit Cell Culture Extract | 0.1 |
| 9 | Ascorbyl Tetraisopalmitate | 0.1 |
| 10 | Phenoxyethanol | Balance |
| 11 | Fragrance | Balance |

Example 24: Shampoo

Using the above silica fine particles (A), a shampoo having the composition shown below was prepared. The preparation method was as follows: Add ingredients (3) to water, mix uniform and heat to 80° C., after the mixture is clear, add ingredients (2) and (5) to (10) to the mixture one by one and confirm the mixture is clear, cool to the room temperature, and add ingredients (11) to (15) one by one and mixed until uniform.

TABLE 21

Shampoo Formulation

| | Ingredients | Amount (Wt. %) |
|---|---|---|
| 1 | Water | Balance |
| 2 | Dipropylene Glycol | 3 |
| 3 | Polyquaternium 10 | 0.4 |
| 5 | Silica fine particles (A) | 5 |
| 6 | Disodium EDTA | 0.05 |
| 7 | Sodium Benzoate | 0.5 |
| 8 | Sodium Laureth Sulfate | 17 |
| 9 | Cocamidopropyl Betaine | 10 |
| 10 | Cocamide MEA | 2 |
| 11 | Phenoxyethanol | Balance |
| 12 | Water, Glycol Distearate, Glycerin, Laureth-4, Cocamidopropyl Betain | 5 |
| 13 | Citric acid | 0.1 |
| 14 | Dimethiconol, Water, Sodium Lauryl Sulfate, Sodium Laureth Sulfate | 2 |
| 15 | Fragrance | Balance |

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

Other Aspects

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the present disclosure has been described in connection with specific aspects thereof, it will be understood that present disclosure is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claimed.

What is claimed is:

1. Silica particles comprising repeating units of $(SiO_{4/2})$, wherein the silica particles are prepared by heating polymethylsilsesquioxane fine particles at a temperature of 500° C. or less in an atmosphere comprising from about 5% to about 15% oxygen, wherein the silica particles have a D90/D10 particle size distribution of about 1.3 or less as measured by particle size analyzer utilizing laser diffraction particle size analysis, wherein the silica particles are spherical and have a sphericity of 0.9 or more, as defined by minor axis/major axis, and wherein the silica particles have a BET surface area from about 0.1 $m^2$/g to about 5 $m^2$/g, and wherein the silica particles are suitable for a personal care formulation.

2. The silica particles of claim 1, wherein the silica particles have a D90/D10 particle size distribution of about 1.0 to about 1.2.

3. The silica particles of claim 1, wherein the silica particles have a median (D50) particle size of about 0.5 μm to about 50 μm.

4. The silica particles of claim 1, wherein the silica particles have sphericity of 0.95 or more as defined by minor axis/major axis.

5. The silica particles of claim 1, wherein the silica particles are non-porous.

6. The silica particles of claim 1, wherein the silica particles are surface-treated with at least one hydrophobicity-imparting agent.

7. The silica particles of claim 6, wherein the hydrophobicity-imparting agent is selected from the group consisting of an alkylsilane, a metal soap, a stearyl modified amino acid, a silicone, fluorinated siliane, natural esters, and combinations thereof.

8. The silica particles of claim 6, wherein the hydrophobicity-imparting agent is hexamethyldisilazane.

9. The silica particles of claim 1, wherein the silica particles have a median (D50) particle size of about 0.5 μm to about 20 μm.

10. A personal care formulation comprising the silica particles of claim 1.

11. The personal care formulation of claim 10 wherein the composition further comprises a preservative, an antioxidant, a binder, an anti-foam agent, an anti-static agent, a colorant, an emulsion stabilizer, an oxidation agent, a propellant, an opacity agent, a UV-filter, a UV-absorber, a denaturing agent, a viscosity regulator, a denaturing agent, a chelating agent, a gum or thickener, an oil, a wax, a fragrance, an essential oil, an emulsifier, a surfactant, and combinations thereof.

12. The personal care formulation of claim 11 wherein the personal care is a deodorant, an antiperspirant, a skin cream, a facial cream, a hair shampoo, a hairconditioner, a mousse, a hair styling gel, a hair spray, a protective cream, a lipstick, a lipcolor, a facial foundations, blushes, makeup, and mascara, a skin care lotion, a moisturizer, a facial treatment, a personal cleanser, a facial cleanser, a bath oil, a perfume, a shaving cream, a pre-shave lotion, an aftershave lotion, a cologne, a sachet, a toothpaste, or a sunscreen.

13. The silica particles of claim 1, wherein the polymethylsilsesquioxane fine particles are heated for about 10 minutes to about 1 hour.

14. The silica particles of claim 1, further comprising reducing the temperature of the polymethylsilsesquioxane fine particles to about 400° C.

15. The silica particles of claim 1, wherein the polymethylsilsesquioxane fine particles are heated for about 10 minutes to about 45 minutes.

16. The silica particles of claim 1, wherein the polymethylsilsesquioxane fine particles are heated in an atmosphere comprising from about 10% to about 15% oxygen.

17. The silica particles of claim 1, wherein the polymethylsilsesquioxane fine particles are heated in an electric furnace, a gas furnace, a far infrared furnace, a medium infrared furnace, or a near infrared furnace.

18. The silica particles of claim 1, wherein the silica particles have a BET surface area from about 0.1 $m^2$/g to about 2.5 $m^2$/g.

19. The silica particles of claim 1, wherein the silica particles are prepared by heating polymethylsilsesquioxane fine particles at a temperature of less than 500° C.

20. Silica particles comprising repeating units of $(SiO_{4/2})$, wherein the silica particles are prepared by heating polymethylsilsesquioxane fine particles at a temperature of less than 500° C. in an atmosphere comprising from about 10% to about 15% oxygen and for a time of from about 10 minutes to about 1 hour, wherein the silica particles have a D90/D10 particle size distribution of about 1.3 or less as measured by particle size analyzer utilizing laser diffraction particle size analysis, wherein the silica particles are spherical and have a sphericity of 0.9 or more, and wherein the silica particles have a BET surface area from about 0.1 $m^2$/g to about 5 $m^2$/g.

21. A white silica powder prepared from the silica particles of claim 20.

* * * * *